United States Patent [19]

Arnegger

[11] 4,252,121
[45] Feb. 24, 1981

[54] SEPARATING DEVICE

[76] Inventor: Richard E. Arnegger, Im Schooren, 8713 Uerikon ZH, Switzerland

[21] Appl. No.: 966,578

[22] Filed: Dec. 5, 1978

[30] Foreign Application Priority Data

Dec. 9, 1977 [CH] Switzerland ............ 15251/77

[51] Int. Cl.³ .................................. A61B 17/14
[52] U.S. Cl. .................................. 128/317
[58] Field of Search .............. 128/317, 91 A, 310; 30/392, 393, 394

[56] References Cited

U.S. PATENT DOCUMENTS

| 2,427,580 | 9/1947 | Stryker | 128/317 |
| 2,557,364 | 6/1951 | Treace | 128/317 |
| 3,044,171 | 7/1962 | Cecere | 128/317 |
| 3,905,374 | 9/1975 | Winter | 128/317 |
| 3,978,862 | 9/1976 | Morrison | 128/317 |

FOREIGN PATENT DOCUMENTS

| 2427716 | 11/1975 | Fed. Rep. of Germany | 128/317 |
| 1455566 | 11/1976 | United Kingdom | 128/317 |

Primary Examiner—Robert W. Michell
Assistant Examiner—T. J. Wallen
Attorney, Agent, or Firm—Donald D. Denton

[57] ABSTRACT

A separating device for manually making separations in solid materials in which a separating blade has a row of teeth that performs oscillating movements with a component directed parallel and a component vertical to the row of teeth in which the amplitude is not greater than twice the distance of neighboring teeth.

12 Claims, 10 Drawing Figures

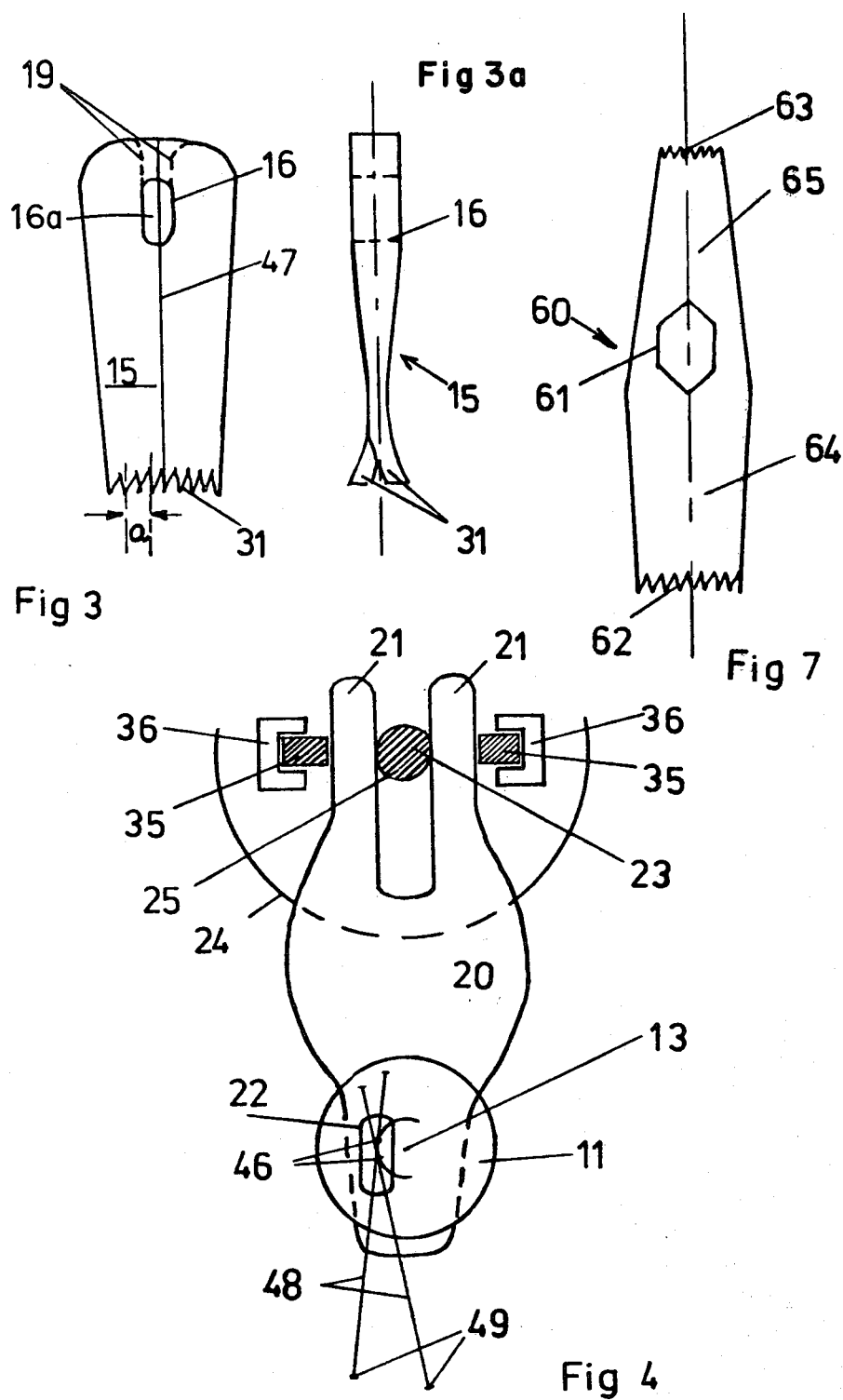

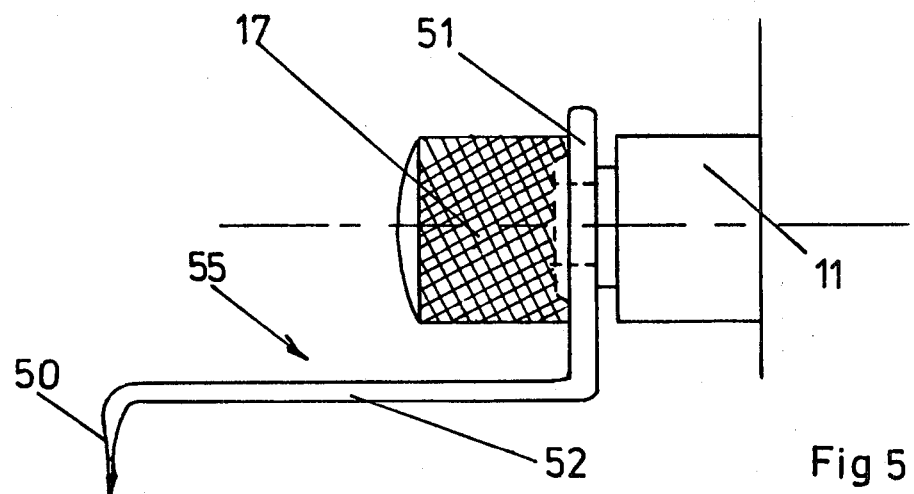
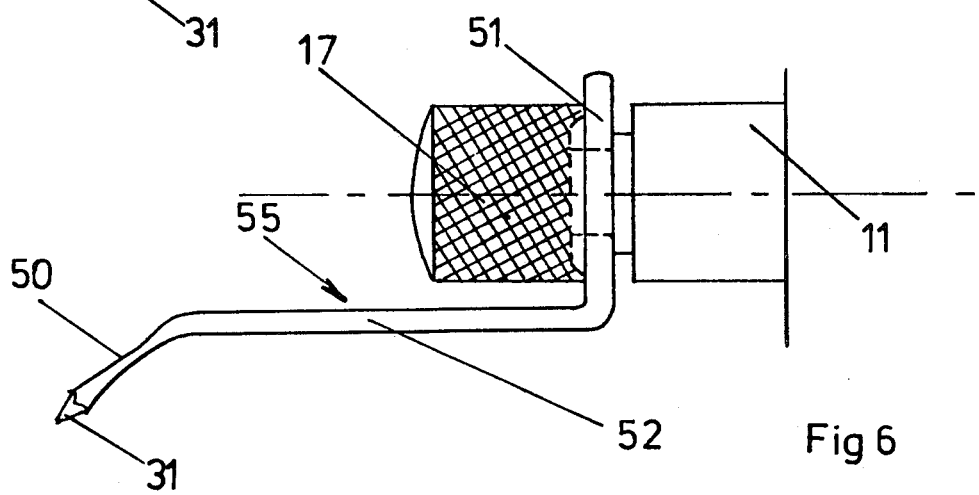

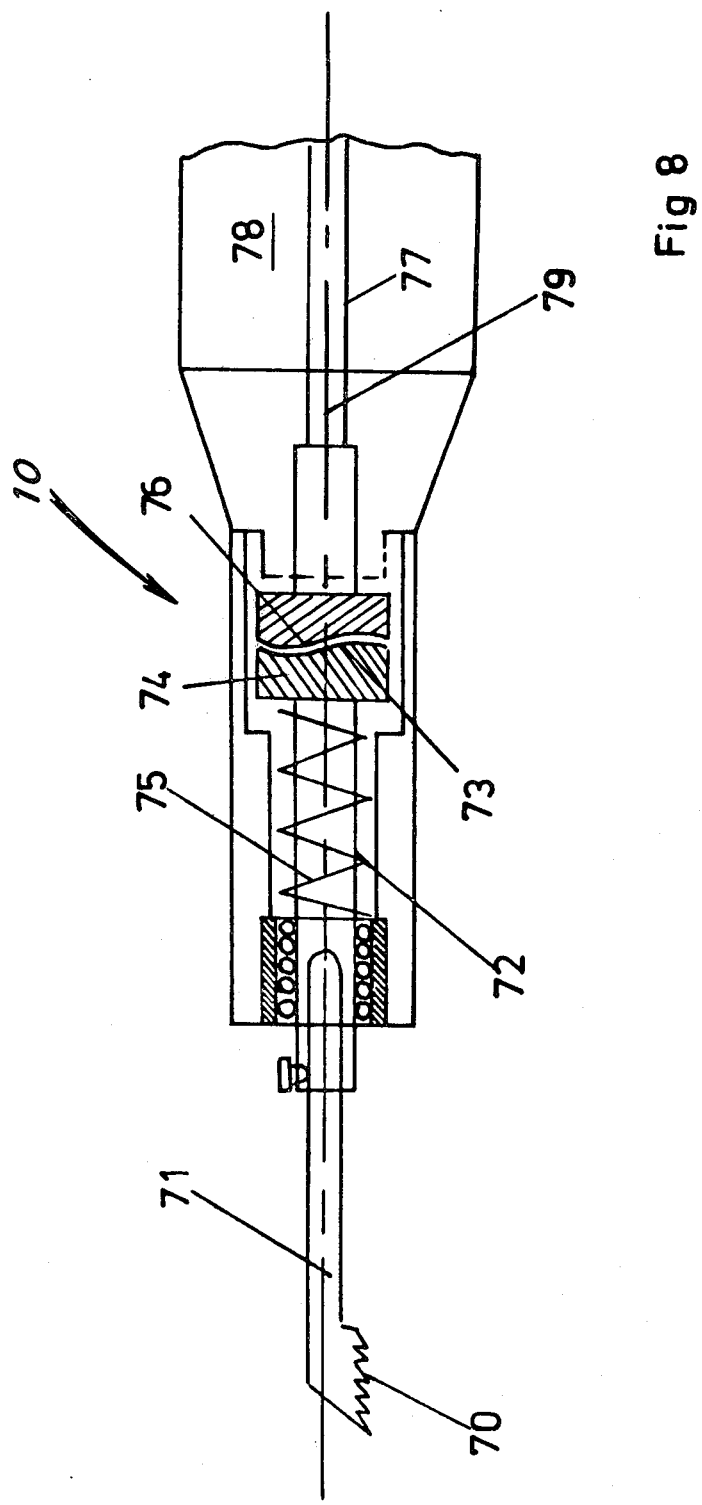

SEPARATING DEVICE

BACKGROUND OF THE INVENTION

The present invention relates to a separating device to produce cuttings manually on solid materials, said separating device being provided with a separating blade, which shows on a part of its periphery a row of teeth that, during operation, make oscillatory movements which comprise a movement component that is substantially parallel and a component substantially vertical to the row of teeth.

It is common knowledge in surgery to make a separation on a bone by sawing, particularly by using an oscillating saw. However, this method of operation has the disadvantage that an unpleasant transmission of vibrations to the hand of the operator is produced. This makes a sensitive working impossible. Furthermore, especially owing to the smearing effect of the living bone and of the bone marrow inside the bone, there will be heat blockings on some parts, which can go up as high as 170° C. and which are the cause of corresponding heat damage. Because of the pasted mass formed by bone meal and bone marrow, the space in between the teeth of the saw will be filled up, and as a consequence, the teeth will lose their cutting ability. This will result in too much pressure being applied to the saw, consequently adding again to the warming up and thus increasing again the wearing of the cutting points of the teeth, so that blades have to be replaced after each operation. This blade replacement proves to be costly. The tendency to press hard on the saw produces moreover an essential danger because, particularly at the end of the cutting process, the surgeon cannot feel the exact moment when the bone will be separated. For this reason and owing to the great oscillating movement of the saw blade, the danger exists that neighboring tissues will be ripped open or hurt by the saw.

SUMMARY OF THE INVENTION

The above mentioned disadvantages are avoided by the present invention which is characterized in that the amplitudes of the component of the movement in the direction parallel to the row of teeth are not greater than twice the distance of neighboring teeth.

At a separating process according to this invention no sawing takes place; it is rather a breakout cutting or a strike separation. Because of this, much less friction will occur so that no substantial warming up of the saw will occur at the place of separation. On account of the small strokes, there is no vibration of the hand tool. Danger of injuries to the doctor or the personnel even while the tool is in operation is eliminated as the separating action will take place only with continuous contact and light pressure.

Because of the small strokes an essential advantage results in that the length of the row of teeth can be adjusted to the particular use. Especially in surgery, injuries of the tissues adjacent to the bone can be practically avoided. For the same reason by this invention it will generally be possible to perform certain methods of cutting which with a sawing movement are not now practicable.

Because vibrations do not occur and as a direct result of the small oscillation strokes of the blade, a very accurate work is possible. The separating device is therefore particularly useful for micro surgery. By applying it in this field, it is of very great advantage if an electrical drive with a micro motor is used. As the micro motor is relatively light and takes up little space, a very handy surgical tool which runs smoothly is produced. Also, it can be held or grasped by the hand in a very easy manner and thus be guided with great sensitivity. In relation thereto today's pneumtically driven sawing motors have a relatively high noise level with the turbine causing a whistling noise. The tubes used for applying the driving fluid are relatively bulky and thick and hinder an easy movement when working with the cutting saw. In addition, by using a driving system based on pressure, the danger of pressure breakdown is relatively high.

BRIEF DESCRIPTION OF THE DRAWINGS

The invention will be explained by the following examples and the figures of the drawing, in which:

FIG. 3 is a front vertical view of a separating blade;

FIG. 3a is a side vertical view of the separating blade;

FIG. 4 is a partial view of an alternate embodiment of a separating device as seen from the front thereof;

FIGS. 5, 6 and 7 are additional embodiments of separating blades;

FIG. 8 is still another embodiment of the separating device; and

DESCRIPTION OF PREFERRED EMBODIMENTS

Figure 1:
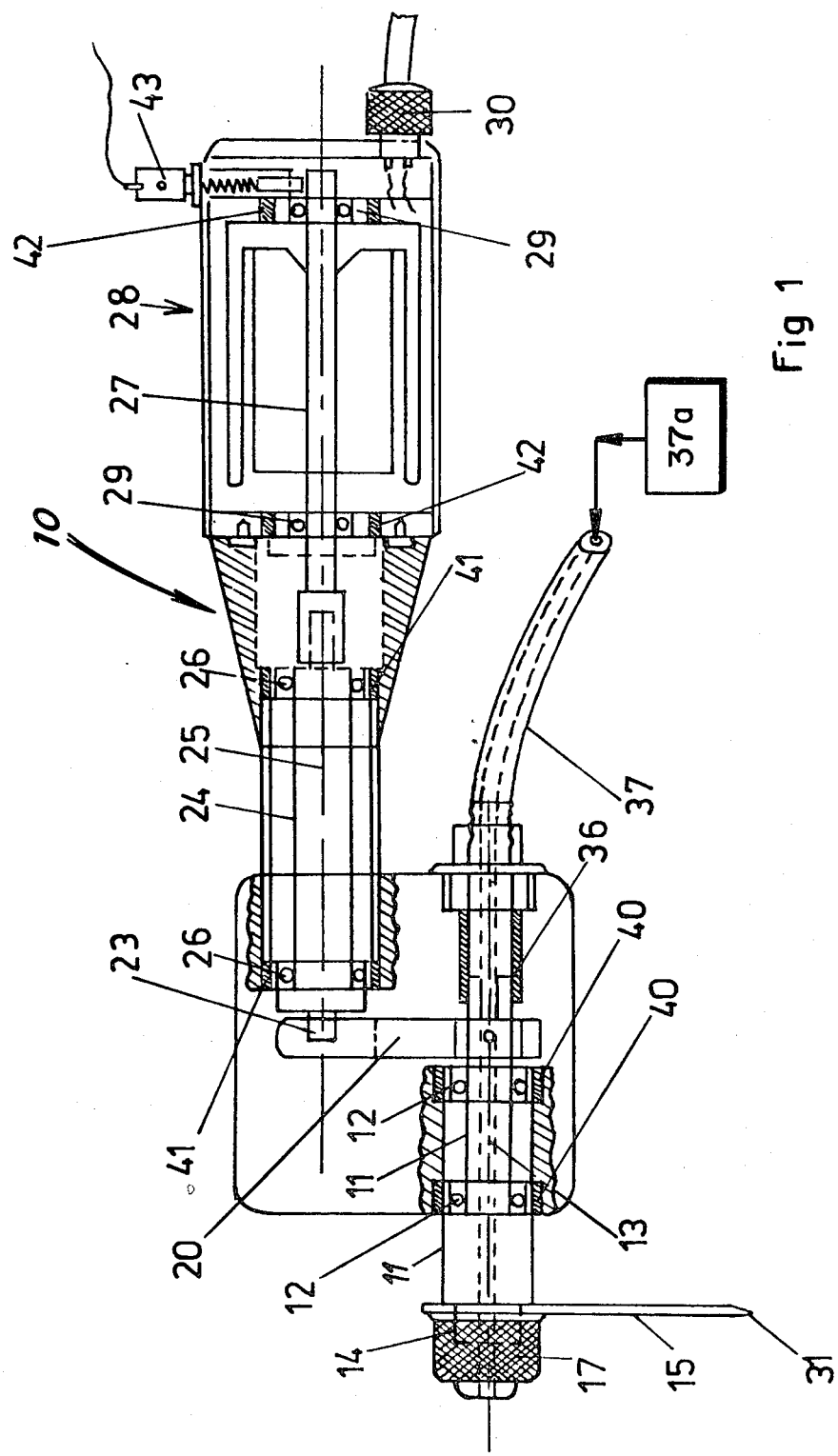
FIG. 1 is a cross-sectional view of the separating device of this invention.
Figure 2:
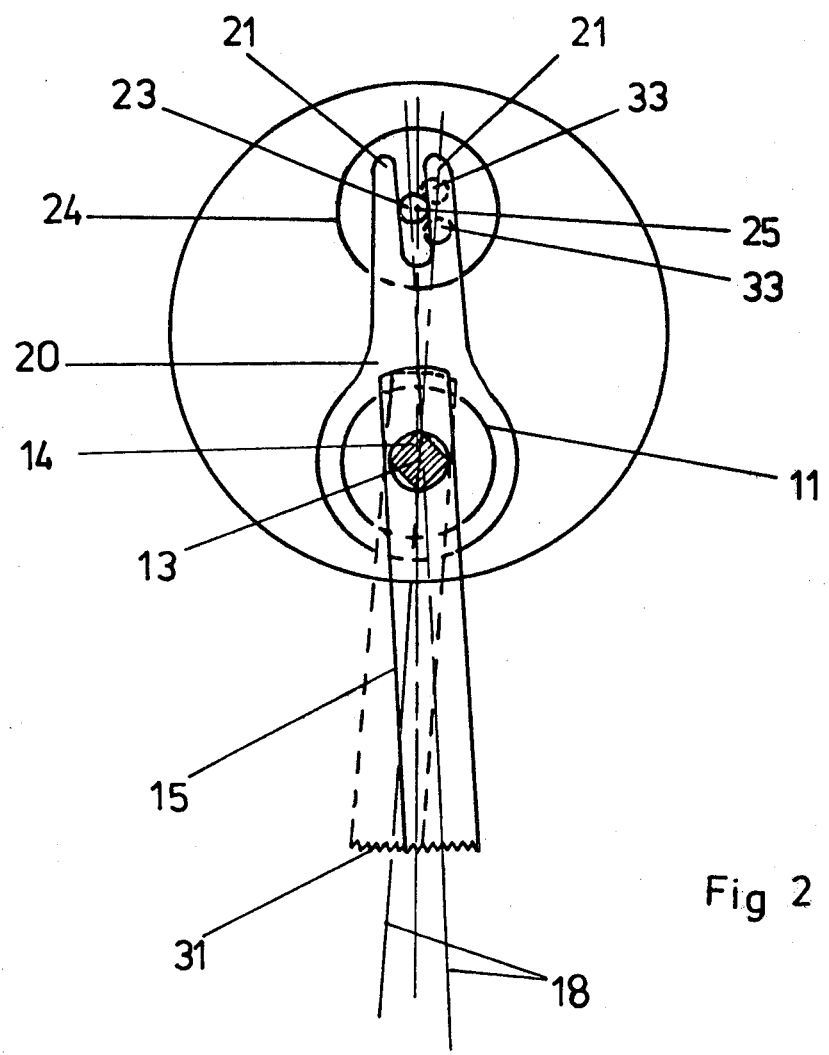
FIG. 2 is an end view as seen from the front, that is as seen from the left side in FIG. 1.

A separating device 10 illustrated in FIGS. 1 and 2 shows an oscillatory member in the form of a turnable shaft or member 11, which is held rotatably mounted in a bearing means in the form of ball bearings 12 in such a way that it can turn in an oscillating manner about an axis 13. On the front side of device 10, the shaft 11 is provided with a projecting blade retaining or holding element or means 14, which is shaped as a square head. A separating blade 15 having a square opening or a clearance therein adapted to receive the square head for mounting of the blade is held in a mounted operable position by a clamp screw 17 which presses the blade 15 in a fixed mounted position against the front of shaft 11.

On the rear side (in FIG. 1, right-hand side) of the shaft 11 there is a driving element for the shaft 11 in the form of a lever 20 operatively fixed to the shaft 11. The lever 20 has two spaced fingers 21 extending parallel to each other (FIG. 2). In between the fingers 21 is positioned a raised round headed bolt or stud 23, which is arranged eccentrically in relation of its axis of rotation 25 on a rotational member or shaft 24. The shaft 24 is rotatably mounted in a bearing means in the form of ball bearings 26 and coupled with a driving spindle 27 of a drive motor or means 28. The driving spindle 27 is rotatable in a bearing means in the form of ball bearings 29. In the case where an electric motor 28 is used as the driving means, as shown in FIG. 1, a plug 30 is provided for making an electrical connection to a supply source of electrical energy for energizing the motor 28.

In FIGS. 3 and 3a there are shown front and side views of a separating blade 15. The blade 15 is provided at one end with a clearance or opening 16 which serves for fixedly mounting it to a blade holding element 16a and in the present case is formed by a longitudinal opening, which fits onto a correspondingly shaped holding element 16a. Instead of a longitudinal opening limited on all sides, there may be provided a slit shaped clearance 19a (shown in the dashed lines on FIG. 3) which provides for ease of assembly or removal of the blade when a change in the type of blade is desired. The blade is held in position by the clamp screw 17. The opposite end of separating blade 15 is provided with a row or set of cutting teeth 31. It is of advantage if the separating blade 15 will be of decreasing thickness in the direction away from the teeth 31 as is shown in FIG 3a.

In operation of the separating device 10, the motor 28 when energized causes the shaft 24 to rotate. This produces a rotation of the bolt 23 around the axis of rotation 25, so that the lever 20 oscillates about the axis 13. These movements cause oscillating movements of the shaft 11 and therewith of the separating blade 15 about the axis 13, causing the teeth 31 to perform back-and-forth strokes. This makes the center-line (47 in FIG. 3) extending in the longitudinal direction of the separating blade 15 to oscillate between the end positions 18. In place of the bolt 23, any other means or device which functions eccentrically can be used to produce the oscillating movement of the separating blade 15 shown in FIG. 3.

According to the invention, the oscillating movements are arranged in such a way that their amplitudes are not greater than the distance a as shown in FIG. 3, that is that they are not greater than twice the distance of neighboring teeth 31. If the device is for micro surgery with a 5 to 10 cm. long separating blade, the amplitudes of the oscillations of the separating blade 15 may, for instance, be about 1.5 millimeter.

It is often of advantage if the amplitudes of the oscillating teeth 31 can be varied. In FIG. 2 an example of such an embodiment is shown. According to this embodiment, three locations 33 are present in which the bolt 23 can be placed. Two such locations are visible in broken line. The bolt 23 is fixed in the third. The three sites 33 are located at three different distances from the axis of rotation 25. Therefore, depending on the location 33 in which the bolt 23 is fixed, the amplitudes of the oscillating teeth 31 will be different. For the sake of better understanding, the eccentricity of the locations 33 is exaggerated in the drawing. Working with various sizes of strokes permits more careful making of a separation.

The shown arrangement is of great advantage in cases where high frequency or icing of the separating blade 15 is used.

Figure 9:
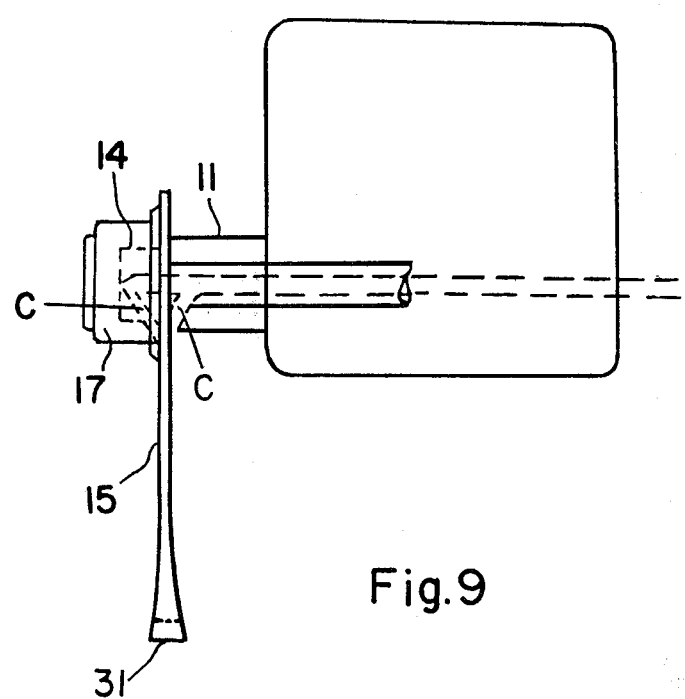
FIG. 9 is a partial view of the separating blade shown in FIG. 1 showing fluid medium conveying channels in a turnable shaft for cooling the separating blade.

In order to produce a refrigeration or an icing of the separating sheet, the oscillatory shaft or member 11 is built as a hollow shaft. At the rear end of this shaft, a tube 36 is connected at one end and a feeding pipe 37 is at the other for supplying a cooling medium (for example carbon dioxide) from a cooling medium supply 37a through the hollow shaft to cool the blade 15. In such an embodiment, the holding element 14 and the hood of the clamp screw 17 are provided with thin bores running in the longitudinal direction of the separating device, so that these parts will be strongly cooled by the flow of the fluid medium thereby providing a high degree of cooling to the separating blade 15. Fluid medium conveying or circulating channels C for cooling the separating blade are provided in shaft 11 to feed the fluid medium from supply 37a to the separating blade 15 (see FIGS. 1 and 9).

Up to now, by using high frequency currents in surgery for blood coagulation, at certain time intervals electrodes have been attached to the operation area. With the separating device according to the present invention, a special electrode at the place of operation is no longer needed because a variable and intermittent supply of high frequency currents can be applied during the entire operation through the separating blade 15 of the separating device. For the purpose of using electrical high frequency currents the set of bearings 12, 26 and 29 are embedded into casings of nonconducting material and by these held in place. Furthermore a plug 43 is provided which serves for connecting the one pole of a source of high frequency. If, for example, a foot operation is taking place, the other pole will be attached to a contact plate fitted to the leg. The high frequency current flows from the current source through the plug 43, the shafts 27, 24, the bolt 23, the lever 20, and the shaft 11 to the separating blade 15. From the blade it flows through the object of operation and, according to the position of the contact plate, through the corresponding part of the leg. The housing of the separating device is insulated from the high frequency current so that the separating device can be held by hand by the surgeon.

In another important embodiment there is superimposed to the already described oscillating movement, which occurs substantially parallel to the row of teeth, a movement which basically takes place vertically to the row of teeth. In FIG. 4 a construction is shown by which such a method of operation is accomplished.

FIG. 4 shows the rotational body 24 with the bolt 23 eccentrically arranged relative to the axis of rotation 25. The oscillatory member 11 with which the lever 20 is operatively connected, shows on its front side the holding element 22 which serves to hold the separating blade. In this example the blade retaining or holding element 22 is arranged eccentrically in relation to the axis 13, around which the oscillations take place. If the lever 20 oscillates, the center of the holding element 22 thus moves back and forth between the position indicated by the points 26. The two straight lines 48 show the extreme positions of the center line 47 of the separating blade shown in FIG. 3. If can be seen that the center of the row of teeth 31 is oscillating back and forth between the points 49. The movement of the center line of the row of teeth 31 as well as the movement of the individual teeth 31 of the separating blade comprise a component in the horizontal and vertical direction. For the sake of a better understanding, in FIG. 4 the different amplitudes of movement have been drawn larger than they actually are.

In the embodiment of FIG. 4 the additional component of movement in the vertical or perpendicular direction to the row of teeth 31 causes the separating blade to cut very easily the material to be separated, so that pressure against the material itself is almost not necessary. By this cutting movement, a further cause for warming up of the place of separation is eliminated.

FIG. 4 also shows an embodiment which results in an especially noiseless and quiet running of the separation device. This is accomplished by two bumper members 35 of elastic material, arranged in such a way that each one elastically contacts the outside of each of the fingers 21. Each of the bumper members 35 is held in place by a fastening element 36.

In this connection it may be mentioned that a swaying movement of the separating blade according to the present invention in the plane defined by the separating blade, that is in the plane of the cut to be made, whereby the center of the row of teeth forms the revolving point, expedites the penetration of the blade into the gap to be formed.

In FIGS. 5 and 6 there are shown examples of differently formed separating blades 55. The oscillating member is again designated by 11 and the clamp screw is designated by 17. The separating blade 55 is made of a longitudinal plate and shows two bent end parts 50 and 51, which have been formed by bending the plate perpendicular to its longitudinal direction at two bending locations. The teeth 31 are at the front end part 50. The separating blade 55 is clamped at the back end part 51. In relation to the straight middle part 52, the back end part 51 forms a right angle. The front end part 50 may, as shown in FIG. 5, also form a right angle or, as shown in FIG. 6, form an obtuse angle with the middle part 52. These forms allow for certain cases a better accessibility or may be the only way to obtain any access to perform the cutting operation.

In another advantageous embodiment, the teeth are formed as so-called pointed roof teeth, that is each tooth is ground on all four sides. In relation to the direction of the row of teeth, the teeth can be ground at an angle which is different from 90° and for example can be ground at an angle of 45° or 135°. The teeth are hereby ground over cross or crosswise. Under these conditions every tooth has the shape of a pyramid with a rectangular base. The working surface of this kind of teeth is relatively small, which again adds to the advantage that, in the separating process, little heat will be produced.

The further example of a separating blade 60 shown in FIG. 7 has a fixing place 61, which in this case is hexagonal (whereby the corresponding holding element 14 must be of hexagonal form). The separating blade 60 has the shape of an elongated plate which is provided on each of two of its opposite ends with a row of teeth 62,63. The separating blade 60 forms two arms 64 and 65 which extend from the opening or place of fixation 61 outwardly and which are of different length. The strokes or amplitudes of the working teeth 62 or 63 are different, depending on whether the teeth 62 or 63 or arms 64 or 65 respectively are selected for working. The teeth 62 or 63 very simply can be put into action alternately during operation by turning the tool, which is grasped by hand, by 180° around its longitudinal axis. In case, for example, a bone operation is executed, one will generally start with a cut performed with small strokes; that means one will start with the teeth 63. Then the separating device will be turned in the hand by 180° around its longitudinal axis and the separating work will be finished with the teeth 62. Getting near the end of the separation process, the separating device will again be turned by 180° and the separation process terminated with the teeth 63. In this manner, a very accurate working is possible and injuries of tissues adjacent to the bone are minimal. It should be obvious that the lengths or the row of teeth 62 and 63 can be different and can be adjusted to special needs or requirements. In general, the longer lever arm will be provided with the longer row of teeth.

In place of a blade 60 with two rows of teeth 62 and 63, two blades can be fixed simultaneously to the holding element 14 or 22, each of which will have only one row of teeth 31. In this case the cutting blades should not be in registry. Preferably they extend with respect to the axis 13 in FIG. 2 in diametrically opposite directions. If the two blades are of different lengths, the strokes will be different.

FIG. 8 shows a separating device 10 with a driving assembly different from the driving as slready shown. Again a row of teeth 70 is provided on a separating blade 71. The blade 71 is held by a rod-like holding element 62, which is movable in the longitudinal direction, that is parallel to the longitudinal axis 79 of the separating device. The holding element 72 is rigidly connected to a member 72 having a curved surface 73, which is biased against the curved surface 76 by a spring 75, fixed on the frontside of a driving shaft 77 of an electrical micro motor 78. On a given angular position the curved surfaces 73 and 76 are fitting snugly and form oppositely curved surfaces. The holding element 72 is not rotatable, so that by the rotation of the driving shaft 77 and under the influence of the spring 75 the holding member 72 is moved in its longitudinal direction back and forth. Thereby the separating blade 71 will be moved in the same way.

While the present invention is particularly useful for the surgical field, it is not limited thereto. It is also useful to make cuts or penetrations in materials of different kinds, especially for material of heterogeneous composition. Correspondingly the use of high frequency as mentioned above is to be understood as an example. In place of high frequency current, alternating current or direct current may be used in certain fields of application. It is obvious that the use of corrugated rows of teeth is also within the scope of this invention.

It will be appreciated that any method of transmission of a cooling fluid to the fluid to the blade 15 may be used as well as any appropriate drive means that may be fluid-powered as well as electrically powered and that such electrically powered drive means can be from either alternating current, direct current, or storage battery energy source.

It will be understood that various changes and/or modifications may be made within the skill of the art without departing from the spirit and scope of the invention illustrated, described, and claimed herein.

What is claimed is:

1. A bone separating device for bone surgery for manually making bone separations, said separating device having a separating blade of flat shape and having positioned along a portion of its periphery a row of cutting teeth intended to perform the actual separating operation; a turnable member operably positioned in said device and oscillating means operably connected to said turnable member for oscillating said turnable member about its axis of rotation during operation of the separating device, said separating blade being operatively fixed to said turnable member with its side faces positioned perpendicular to the said axis of rotation of said turnable member to cause during the rotation of the turnable member the cutting teeth on the blade to oscillate in a path parallel to side faces of the blade, amplitudes of the oscillations of the cutting teeth being not greater than twice the distance of neighboring teeth; and a portion of the thickness of the separating blade decreased in the direction away from the base of said cutting teeth.

2. The separating device according to claim 1 in which the separating blade is detachably held at a fixing location by a blade retaining means which is attached to a front side of a turnable member that oscillates about its longitudinal axis and a rotatable eccentric means which is operatively coupled to said turnable member to cause said turnable member to execute oscillating movements when said eccentric means is rotated.

3. The separating device according to claim 2 in which the blade retaining element holding the separating blade is eccentrically arranged in relation to the axis of said turnable member.

4. The separating device according to claim 2 in which said eccentric means comprises a bolt head attached to a rotational member, said bolt head being interlinked with a lever being rigidly connected with said turnable member and serving to pivot said turnable member, the rotational member being provided with a plurality of locations for selectively attaching the bolt head, the distances of said locations from the axis of rotation of said rotational member being different from each other.

5. The separating device according to claim 2 in which the blade holding element is of a multiangular form and the separating blade at the place of fixation has an opening matching exactly with said multiangular form.

6. The separating device according to claim 1 in which the oscillating means for the oscillation of the separating blade is driven by an electrical micro motor.

7. The separating device according to claim 1 in which the teeth of the separating blade are ground cross-wise as roof point teeth having the form of a pyramid with four sides.

8. The bone separating device according to claim 1 in which a plane passing through the middle of said row of teeth and arranged perpendicular to said row of teeth and to the side faces of said blade has a finite distance from said axis of rotation so that during oscillations of said blade the movement of the cutting teeth comprises a component which is parallel and a component which is directed vertically to the row of teeth, the first-named component being larger than the other one.

9. A bone separating device for bone surgery for manually making bone separations, said separating device having a separating blade of flat shape and having positioned along a portion of its periphery a row of cutting teeth intended to perform the actual separating operation; a turntable member operably positioned in said device and oscillating means operably connected to said turnable member for oscillating said turnable member about its axis of rotation during operation of the separating device, said separating blade being operatively fixed to said turnable member with its side faces positioned perpendicular to the said axis of rotation of said turnable member to cause during the rotation of the turnable member the cutting teeth on the blade to oscillate in a path parallel to side faces of the blade, said separating blade detachably held at a fixing location by a blade retaining means which is attached to a front side of a turnable member that oscillates about its longitudinal axis and a rotatable eccentric means which is operatively coupled to said turnable member to cause said turnable member to execute oscillating movements when said eccentric means is rotated, said separating blade electrically insulated from the housing and operatively connectable to a current source.

10. The separating device according to claim 9 in which said current source is of high frequency.

11. The separating device according to claim 9 in which the turnable member, the rotational member carrying the eccentric means, and the rotor of a motor driving the rotational member are each rotatably supported in bearing means which are embedded in an electrically insulating material so that there is formed an electrically conducting path to the separating blade through an electrical connector plug for providing a source of electrical current to the blade.

12. A bone separating device for bone surgery for manually making bone separations, said separating device having a separating blade of flat shape and having positioned along a portion of its periphery a row of cutting teeth intended to perform the actual separating operation; a turnable member operably positioned in said device and oscillating means operably connected to said turnable member for oscillating said turnable member about its axis of rotation during operation of the separating device, said separating blade being operatively fixed to said turnable member with its side faces positioned perpendicular to the said axis of rotation of said turnable member to cause during the rotation of the turnable member the cutting teeth on the blade to oscillate in a path parallel to side faces of the blade, said separating blade detachably held at a fixing location by a blade retaining means which is attached to a front side of a turnable member that oscillates about its longitudinal axis and a rotatable eccentric means which is operatively coupled to said turnable member to cause said turnable member to execute oscillating movements when said eccentric means is rotated, said turnable member provided with a bore, which at the end opposite the separating blade is connectable by a conduit means to a source of cooling medium, and from which bore at its end at the location of the separating blade circulation channels are provided in the blade retaining means for conveying the cooling medium in contact with the separating blade.

* * * * *